US010881637B2

(12) United States Patent
Solomon

(10) Patent No.: US 10,881,637 B2
(45) Date of Patent: Jan. 5, 2021

(54) INTRANASAL AND TRANSDERMAL ADMINISTRATION OF KAPPA-OPIOID-RECEPTOR AGONISTS: SALVINORIN A FOR THE TREATMENT OF NEUROPSYCHIATRIC AND ADDICTIVE DISORDERS

(71) Applicant: Atlee Solomon, Vienna, VA (US)

(72) Inventor: Atlee Solomon, Vienna, VA (US)

( * ) Notice: Subject to any disclaimer, the term of this patent is extended or adjusted under 35 U.S.C. 154(b) by 60 days.

(21) Appl. No.: 15/354,078

(22) Filed: Nov. 17, 2016

(65) Prior Publication Data

US 2017/0135984 A1 May 18, 2017

Related U.S. Application Data

(60) Provisional application No. 62/256,409, filed on Nov. 17, 2015.

(51) Int. Cl.
| A61K 31/366 | (2006.01) |
| A61K 9/00 | (2006.01) |
| A61K 36/185 | (2006.01) |
| A61K 31/137 | (2006.01) |
| A61K 36/537 | (2006.01) |

(52) U.S. Cl.
CPC .......... A61K 31/366 (2013.01); A61K 9/0014 (2013.01); A61K 9/0043 (2013.01); A61K 31/137 (2013.01); A61K 36/185 (2013.01); A61K 36/537 (2013.01)

(58) Field of Classification Search
CPC .. A61K 31/137; A61K 31/366; A61K 36/185; A61K 36/537; A61K 9/0014; A61K 9/0043; A61K 31/135; A61K 31/352
See application file for complete search history.

(56) References Cited

U.S. PATENT DOCUMENTS

| 8,449,908 B2* | 5/2013 | Stinchcomb | A61K 9/0014 424/443 |
| 8,492,564 B2 | 7/2013 | Beguin et al. | |
| 8,980,940 B2* | 3/2015 | Rossi | A61K 9/4858 514/453 |
| 2009/0311347 A1* | 12/2009 | Oronsky | A61K 45/06 424/722 |
| 2011/0038807 A1* | 2/2011 | Papolos | A61K 31/135 424/45 |
| 2011/0245287 A1* | 10/2011 | Holaday | A61K 31/485 514/282 |
| 2012/0010219 A1* | 1/2012 | Beguin | C07D 311/92 514/255.05 |
| 2015/0132282 A1* | 5/2015 | Finzi | A61K 31/5513 424/94.67 |
| 2015/0196501 A1* | 7/2015 | Erickson | A61K 31/135 514/647 |
| 2016/0015818 A1* | 1/2016 | Taha | A61K 31/135 514/217 |
| 2016/0076098 A1* | 3/2016 | Ajit | C12Q 1/6883 514/647 |
| 2018/0125777 A1* | 5/2018 | Lindsay | A61K 9/009 |

OTHER PUBLICATIONS

Kluger et al. (Mov Disord. Mar. 2015 ; 30(3): 313-327) (Year: 2015).*
Murrough et al., "Rapid and Longer-Term Antidepressant Effects of Repeated Ketamine Infusions in Treatment-Resistant Major Depression", Biol Psychiatry 74:250-256 (2013).
Kivel et al., "Salvinorin a analogs and other kappa opioid receptor compounds as treatments for cocaine abuse", Adv. Pharmacol. 69:481-511 (2014).
Lally et al., "Anti-anhedonic effect of ketamine and its neural correlates in treatment-resistant bipolar depression", Transl Psychiatry, 2014, vol. 4, e469, 9 pps.
MacLean et al., "Dose-related effects of salvinorin a in humans: dissociative, hallucinogenic, and memory effects", Psychopharmacology, 226:381-392 (2013).
Mowry et al., "Acute Physiologic and Chronic Histologic Changes in Rats and Mice Exposed to the Unique Hallucinogen Salvinorin A.", J. Psychoactive Drugs, 35:379-382 (2003).
Pastora, "Salvia divinorum Epling et Jativa-M.", Frantisek Stary Giftpflanzen (1983), 4 pps.
Abelaira, et al., "Animal Models as tools to study the pathophysiology of depression", Revista Brasileira de Psiquiatria, 35:S112-S120 (2013).
Abulseoud et al., "Lateral hypothalmic kindling induces manic-like behavior in rats: a novel animal model", International Journal of Bipolar Disorders, 2(7): 12 pages (2014).
Afridi et al., "A randomized controlled trial of intranasal ketamine in migraine with prolonged aura", Neurology, 80:642-647 (2013).
Andrade, "Intranasal Drug Delivery in Neuropsychiatry: Focus on Intranasal Ketamine for Refractory Depression", J. Clin. Psychiatry, 76(5):628-631 (2015).
Arrant et al., "Use of the light/dark test for anxiety in adult and adolescent male rats", Behavioural Brain Research 256: 119-127 (2013).
Braida et al., "Potential anxiolytic- and antidepressant-like effects of salvinorin A, the main active ingredient of salvia divinorum, in rodents", British Journal of Pharmacology, 157:844-853 (2009).
Belelli, et al., "Extrasynaptic GABAA Receptors: Form, Pharmacology, and Function", The Journal of Neuroscience 29(41): 12757-12763 (2009).
Bitter et al., "Nasal Drug Delivery in Humans", Curr. Prol. Dermatol. 40:20-35 (2011).
Bogdanova et al., "Factors influencing behavior in the forced swim test", Physiology and Behavior, 118: 227-239 (2013).
Bourin, "Animal models for screening anxiolytic-like drugs: a perspective", Dialogues in Clinical Neuroscience 17:295-303 (2015).

(Continued)

Primary Examiner — Snigdha Maewall
(74) Attorney, Agent, or Firm — Elie Gendloff; Gendloff IP

(57) ABSTRACT

Methods of treating neuropsychiatric disorders including affective disorders and addiction involve intranasal or transdermal administration of a substantially selective kappa-opioid-receptor agonist that is also a partial D2 agonist, such as the compound salvinorin A. Also disclosed are intranasal, transdermal and/or inhalation systems for delivering the kappa-opioid-receptor agonist.

18 Claims, No Drawings

(56) References Cited

OTHER PUBLICATIONS

Gehrke et al., "Effects of acute and repeated administration of salvinorin A on dopamine function in the rat dorsal striatum", Psychopharmacology, 197(3):509-517 (2008).
Campos et al., "Animal models of anxiety disorders and stress", Revista Brasileira de Psiquiatria 35:S101-S111 (2013).
Clark et al., "Treatment-refractory depression: a case of successful treatment with intranasal ketamine 10%", Ann Clin Psychiatry 26(2):145 (2014).
Cunningham et al., "Neuropharmacology of the Naturally Occurring κ-Opioid Hallucinogen Salvinorin A," Pharmacol Rev 63(2):316-347 (2011).
Dhuria et al., "Intranasal delivery to the central nervous system: mechanisms and experimental considerations", J Pharm Sci., 99(4):1654-1673 (2011).
Djupesland et al., "The nasal approach to delivering treatment for brain diseases: an anatomic, physiologic, and delivery technology overview", Therapeutic Delivery 5(6):709-733 (2014).
Evans et al., "Pharmacology of the ß-Carboline FG-7142, a Partial Inverse Agonist at the Benzodiazepine Allosteric Site of the GABAA Receptor: Neurochemical, Neurophysiological, and Behavioral Effects", CNS Drug Reviews 13(4): 475-501 (2007).
Galaj et al., "Microinjections of a dopamine D1 receptor antagonist into the ventral tegmental area block the expression of cocaine conditioned place preference in rats", Beh Brain Research. 272: 279-285 (2014).
Giroud et al., "Salvia divinorum: an hallucinogenic mint which might become a new recreational drug in Switzerland", Forensic Sci. Int. 112:143-150 (2000).
Gould et al., "Animal models of bipolar disorder and mood stabilizer efficacy: a critical need for improvement", Neurosci. Biobehav. Rev. 31:825-831 (2007).
Hanes, "Antidepressant Effects of the Herb Salvia Divinorum: A Case Report", Journal of Clinical Psychopharmacology, 21(6):634-635 (2001).
Harden et al., "Antidepressive effects of the κ-opioid receptor agonist Salvinorin A in a rat model of anhedonia", Behav Pharmacol. 23(7):710-715 (2012).
Ita, "Transdermal Delivery of Drugs with Microneedles—Potential and Challenges", Pharmaceutics 7, 90-105 (2015).
Johnson et al., "Human psychopharmacology and dose-effects of Salvinorin A, a kappa-opioid agonist hallucinogen present in the plant Salvia divinorum", Drug Alcohol Depend, 115:150-155 (2011).
Krishnan et al., "Animal models of depression: molecular perspectives", Curr. Top. Behav. Neurosci. 7:121-147 (2011).
Lapidus et al., "A randomized controlled trial of intranasal ketamine in major depressive disorder", Biol Psychiatry 76:970-976 (2014).
Lopez-Lopez et al., "Chronic unpredictable mild stress generates oxidative stress and systemic inflammation in rats", Physiology & Behavior, 161: 15-23 (2016).
Maqueda et al., "Salvinorin-A Induces Intense Dissociative Effects, Blocking External Sensory Perception and Modulating Interoception and Sense of Body Ownership in Humans", Int. J. of Neuropsychopharmacol., 1-14 (EPub ahead of print)(2015).
Mendelson et al., "Lack of effect of sublingual Salvinorin A, a naturally occurring kappa opioid, in humans: a placebo-controlled trial", Psychopharmacol, 214:933-939 (2011).
Morani et al., "Effect of kappa-opioid receptor agonists U69593, U50488H, spiradoline and Salvinorin A on cocaine-induced drug-seeking in rats", Pharmacal Biochem Behav 94: 244-249 (2009).
Orton et al., "Salvinorin A: A Mini Review of Physical and Chemical Properties Affecting Its Translation from Research to Clinical Applications in Humans", Transl. Perioper. Pain Med., 1(1):9-11 (2014).
Ott, "Ethnopharmacognosy and Human Pharmacology of Salvia divinorum and Salvinorin A", Curare 18(1):103-129 (1995).
Papp et al., "Pharmacological validation of the chronic mid stress model of depression", Eur J Pharmacology. 296:129-136 (1996).
Pastore et al., "Transdermal patches: history, development and pharmacology", British J. Pharmacol. 172 (9):2179-2209 (2015).
Paudel et al., "Challenges and opportunities in dermal/transdermal delivery", Ther. Deliv.1(1):109-131 (2010).
Pellow et al., "Anxiolytic and Anxiogenic Drug Effects on Exploratory Activity in an Elevated Plus-Maze: a Novel Test of Anxiety in the Rat", Pharmacology Biochemistry & Behavior 24: 525-529 (1986).
Prevatt-Smith et al, "Potential Drug Abuse Therapeutics Derived from the Hallucinogenic Natural Product Salvinorin A", Med. Chem. Comm. 2:1217-1222 (2011).
Roth et al., "Salvinorin A: A potent naturally occurring non-nitrogenous κ opioid selective agonist", PNAS 99 (18):11934-11939 (2004).
Seeman et al., "Dopamine D2High receptors stimulated by phencyclidines, lysergic acid diethylamide, Salvinorin A, and modafinil", Synapse 63:698-704 (2009).
Siebert, "Salvia divinorum and Salvinorin A: new pharmacologic findings", J Ethnopharmacol. 43:53-56 (1994).
Thompson et al., "Tracazolate Reveals a Novel Type of Allosteric Interaction with Recombinant y-Aminobutyric AcidA Receptors", Molecular Pharmacology 61(4): 861-869 (2002).
Yatham et al., "Brain serotonin-2 receptors in acute mania", The British J. Psych. 196:47-51 (2010).
Ebner et al., "Depressive-like effects of the kappa opioid receptor agonist salvinorin A are associated with decreased phasic dopamine release in the nucleus accumbens", Psychopharmacology 210:241-252 (2010).
Chartoff et al., "Exposure to the Selective κ-Opioid Receptor Agonist Salvinorin A Modulates the Behavioral and Molecular Effects of Cocaine in Rats", Neuropsychopharmacology, 33(11):2676-2687 (2008).
Butelman et al., "Salvinorin A, a kappa-opiod receptor agonist hallucinogen: pharmacology and potential template for novel pharmacotherapeutic agents in neuropsychiatric disorders", Frontiers in Pharmacology 6(190):7 pps (2015).
Butelman et al., "The discriminative effects of hte k-opioid hallucinogen salvinorin A in nonhuman primates: dissociation from classic hallucinogen effects", Psychopharmacology, 210(2):253-262 (2010).
Berman et al., "Antidepressant effects of ketamine in depressed patients", Biological Psychiatry, 47:351-354 (2000).
Naylor et al., "Self-administration of oxycondone alone or as a mixture with the kappa agonist, salvinorin a, by monkeys under a progressive ratio schedule of reinforcement", Abstracts, Drug and Alcohol Dependence, (2015) 146: e48-e49.
Nemeth et al., "Role of kappa-opioid receptors in the effects of salvinorin a and ketamine on attention in rats", Psychopharmacology 210(2):263-274 (2010).
Walentiny et al., "Kappa opioid mediation of cannabinoid effects of the potent hallucinogen, salvinorin A, in rodents", Psychopharmacology 210:275-284 (2010).

* cited by examiner

INTRANASAL AND TRANSDERMAL ADMINISTRATION OF KAPPA-OPIOID-RECEPTOR AGONISTS: SALVINORIN A FOR THE TREATMENT OF NEUROPSYCHIATRIC AND ADDICTIVE DISORDERS

CROSS-REFERENCE TO RELATED APPLICATIONS

This application claims the benefit of U.S. Provisional Application No. 62/256,409, filed Nov. 17, 2015, and incorporated by reference herein in its entirety.

BACKGROUND OF THE INVENTION (1) Field of the Invention

The present invention is related to the treatment of neuropsychiatric conditions with kappa-opioid-receptor agonists and, in particular, to intranasal, transdermal and inhalation systems and methods of administration of kappa-opioid-receptor agonists for the treatment of neuropsychiatric conditions.

(2) Description of the Related Art

Salvinorin A is a naturally occurring psychoactive compound isolated from Salvia divinorum. Studies have demonstrated that salvinorin A is a uniquely selective kappa-opioid-receptor agonist with no significant effect on a battery of 50 other receptors, transporters and ion channels including mu- and delta-opioid receptors (Roth et al., 2004). In addition to having kappa-opioid-agonist activity, salvinorin A has been found to be a D2 receptor partial agonist (Seeman et al., 2009). Notably, salvinorin A has been shown to have no significant effect on $5HTP_{2A}$ receptors and as a result, administration of salvinorin A to a subject would not be expected to produce mania (Yatham et al., 2010). Recent studies have suggested that salvinorin A may have anti-depression and anti-addiction properties among other potentially beneficial properties (Morani et al., 2009; Prevatt-Smith et al, 2011; Harden et al., 2012; Orton et al., 2014).

Several routes of administration have been used for Salvia divinorum and for salvinorin A with varying degrees of success. In traditional practice among the Mazatec people of Mexico, Salvia divinorum was ingested by chewing the fresh leaves as a quid or by smoking (Valdes, 1994; Siebert, 1994). Absorption upon chewing is apparently by the buccal route in as much as encapsulated salvinorin A is inactive when administered orally (Siebert, 1994; Ott, 1995). Sublingual administration has generally yielded inconsistent results or no absorption at all (Siebert, 1994; Mendelson et al., 2011). The most common route of administration of Salvia divinorum has been inhalation by smoking the leaves (Giroud et al., 2000). More recently, the inhalation route of administration has been used for the active component, salvinorin A, in human subjects (Johnson et al., 2011; Maqueda et al., 2015).

Although infrequently used, the intranasal route of administration has been proposed for use in pharmacologic treatment of neuropsychiatric conditions. Potential advantages of intranasal administration are rapid onset of action, the ability to bypass the blood-brain barrier, improvement in bioavailability and avoidance of parenteral administration (Andrade, 2015). Nevertheless, there are numerous challenges and potential problems that have limited the use of intranasal administration of drugs for the treatment of neuropsychiatric conditions (Dhuria, 2010; Djupesland, 2014). In spite of this, the neuropsychiatric drug ketamine is currently under experimental investigation using the intranasal route of administration for treatment of acute and chronic pain, autism, depression and other conditions (Afridi, 2013; Yeaman, 2014; Clark, 2014, Lapidus, 2014; Graudins, 2015). Naltrexone can potentiate the effects of ketamine (Krystal et al., 2006).

Similar to the intranasal route of administration, transdermal administration presents challenges and only a few medications can be delivered through the transdermal route in therapeutic amounts (Paudel, 2010; Ita, 2015).

As noted above, numerous studies have evaluated different routes of administration for salvinorin A. Nevertheless, none of the routes of administration that have been studied are particularly suited for use in neuropsychiatry.

BRIEF SUMMARY OF THE INVENTION

Accordingly, the applicant herein has invented an intranasal system and method and a transdermal system and method for administration of kappa-opioid-selective agonists such as salvinorin A, for the treatment of neuropsychiatric conditions.

Thus in various embodiments, the present invention involves a method of treating an affective disorder in a patient in need thereof. The method may comprise administering intranasally to the patient, a therapeutically effective amount of a substantially selective kappa-opioid-receptor agonist in a pharmaceutically acceptable preparation. In various embodiments, the kappa-opioid-receptor agonist may be devoid of activity on $5HT_2$ receptors, in particular $5HT_{2A}$ receptors, such that it produces substantially no manic effect. In various embodiments, the kappa-opioid-receptor agonist also has D2 agonist activity and, in particular, partial D2 agonist activity. In certain embodiments, the kappa-opioid-receptor agonist may be salvinorin A. Administration may be with an intranasal delivery device.

In various embodiments, the affective disorder may be depression, bipolar disorder or anxiety disorder.

In various aspects of this embodiment, the kappa-opioid-receptor agonist may be administered with either or both of a cannabinoid compound and ketamine in a pharmaceutically acceptable preparation. The pharmaceutically acceptable preparation for the cannabinoid compound and/or ketamine may include the same carrier system in which the kappa-opioid-receptor agonist is administered and the substances may be administered together or separately in any combination thereof. Alternatively, the carrier system for the cannabinoid compound and/or ketamine may be different from that of the kappa-opioid-receptor agonist and the substances may be administered separately. In some embodiments, naltrexone is included.

In various embodiments, the present invention may involve a method of treating addiction in a subject in need thereof. The method may comprise administering intranasally to the patient, a therapeutically effective amount of a substantially selective kappa-opioid-receptor agonist in a pharmaceutically acceptable preparation. In various embodiments, the kappa-opioid-receptor agonist may be devoid of activity on $5HT_2$ receptors, in particular $5HT_{2A}$ receptors, such that it produces substantially no manic effect. In various embodiments, the kappa-opioid-receptor agonist also has D2 agonist activity and, in particular, partial D2 agonist activity. In certain embodiments, the kappa-opioid-receptor agonist may be salvinorin A. Administration may be with an intranasal delivery device.

In various embodiments, the addiction may be an addiction to nicotine, cocaine, opioids, amphetamine, methamphetamine, ethanol, heroin, morphine, phencyclidine, 3,4-methylenedioxy-methamphetamine, as well as other addictive substances and addictive behaviors.

In various aspects of this embodiment, the kappa-opioid-receptor agonist may be administered with either or both of a cannabinoid compound and ketamine in a pharmaceutically acceptable preparation. The pharmaceutically acceptable preparation for the cannabinoid compound and/or ketamine may include the same carrier system in which the kappa-opioid-receptor agonist is administered and the substances may be administered together or separately in any combination thereof. Alternatively, the carrier system for the cannabinoid compound and/or ketamine may be different from that of the kappa-opioid-receptor agonist and the substances may be administered separately. In some embodiments, naltrexone is included.

In yet another embodiment, the present invention may involve an intranasal delivery system. The system may comprise an intranasal delivery device and a therapeutically effective amount of a substantially selective kappa-opioid-receptor agonist in a pharmaceutically acceptable preparation. In various embodiments, the kappa-opioid-receptor agonist may be devoid of activity on $5HT_2$ receptors, in particular $5HT_{2A}$ receptors, such that it does not produce mania. In various embodiments, the kappa-opioid-receptor agonist also has D2 agonist activity and, in particular, partial D2 agonist activity. In certain embodiments, the kappa-opioid-receptor agonist may be salvinorin A.

In various aspects of this embodiment, the system may include, in addition to the kappa-opioid-receptor agonist, either or both of a cannabinoid compound and ketamine in a pharmaceutically acceptable preparation. The pharmaceutically acceptable preparation for the cannabinoid compound and/or ketamine may include the same carrier system in which the kappa-opioid-receptor agonist is administered and the substances may be administered together or separately in any combination thereof. Alternatively, the carrier system for the cannabinoid compound and/or ketamine may be different from that of the kappa-opioid-receptor agonist and the substances may be administered separately. In some embodiments, naltrexone is included.

In various other embodiments, the present invention may involve an inhalation delivery system. The system may comprise an inhalation delivery device and a therapeutically effective amount of a substantially selective kappa-opioid-receptor agonist in a pharmaceutically acceptable preparation. In various embodiments, the kappa-opioid-receptor agonist may be devoid of activity on $5HT_2$ receptors, in particular $5HT_{2A}$ receptors, such that it produces substantially no manic effect. In various embodiments, the kappa-opioid-receptor agonist also has D2 agonist activity and, in particular, partial D2 agonist activity. In certain embodiments, the kappa-opioid-receptor agonist may be salvinorin A.

In various aspects of this embodiment, the system may include, in addition to the kappa-opioid-receptor agonist, either or both of a cannabinoid and ketamine in a pharmaceutically acceptable preparation. The pharmaceutically acceptable preparation for the cannabinoid compound and/or ketamine may include the same carrier system in which the kappa-opioid-receptor agonist is administered and the substances may be administered together or separately in any combination thereof. Alternatively, the carrier system for the cannabinoid compound and/or ketamine may be different from that of the kappa-opioid-receptor agonist and the substances may be administered separately. In some embodiments, naltrexone is included.

In various other embodiments, the present invention involves a method of treating an affective disorder in a patient in need thereof. The method may comprise administering transdermally to the patient, a therapeutically effective amount of a substantially selective kappa-opioid-receptor agonist in a pharmaceutically acceptable preparation. In various embodiments, the kappa-opioid-receptor agonist may be devoid of activity on $5HT_2$ receptors, in particular $5HT_{2A}$ receptors, such that it produces substantially no manic effect. In various embodiments, the kappa-opioid-receptor agonist also has D2 agonist activity and, in particular, partial D2 agonist activity. In certain embodiments, the kappa-opioid-receptor agonist may be salvinorin A. Administration may be with a transdermal delivery device or system.

In various embodiments, the affective disorder may be depression, bipolar disorder or anxiety disorder.

In various aspects of this embodiment, the kappa-opioid-receptor agonist may be administered with either or both of a cannabinoid compound and ketamine in a pharmaceutically acceptable preparation. The pharmaceutically acceptable preparation for the cannabinoid compound and/or ketamine may include the same carrier system in which the kappa-opioid-receptor agonist is administered and the substances may be administered together or separately in any combination thereof. Alternatively, the carrier system for the cannabinoid compound and/or ketamine may be different from that of the kappa-opioid-receptor agonist and the substances may be administered separately. In some embodiments, naltrexone is included.

In various embodiments, the present invention may involve a method of treating addiction in a subject in need thereof. The method may comprise administering transdermally to the patient, a therapeutically effective amount of a substantially selective kappa-opioid-receptor agonist in a pharmaceutically acceptable preparation. In various embodiments, the kappa-opioid-receptor agonist may be devoid of activity on $5HT_2$ receptors, in particular $5HT_{2A}$ receptors, such that it produces substantially no manic effect. In various embodiments, the kappa-opioid-receptor agonist also has D2 agonist activity and, in particular, partial D2 agonist activity. In certain embodiments, the kappa-opioid-receptor agonist may be salvinorin A. Administration may be with a transdermal delivery device or system.

In various embodiments, the addiction may be an addiction to nicotine, cocaine, opioids, amphetamine, methamphetamine, ethanol, heroin, morphine, phencyclidine, 3,4-methylenedioxy-methamphetamine, as well as other addictive substances and addictive behaviors.

In various aspects of this embodiment, the kappa-opioid-receptor agonist may be administered with either or both of a cannabinoid compound and ketamine in a pharmaceutically acceptable preparation. The pharmaceutically acceptable preparation for the cannabinoid compound and/or ketamine may include the same carrier system in which the kappa-opioid-receptor agonist is administered and the substances may be administered together or separately in any combination thereof. Alternatively, the carrier system for the cannabinoid compound and/or ketamine may be different from that of the kappa-opioid-receptor agonist and the substances may be administered separately. In some embodiments, naltrexone is included.

In yet another embodiment, the present invention may involve a transdermal delivery system. The system may comprise a transdermal delivery device and a therapeutically effective amount of a substantially selective kappa-opioid-receptor agonist in a pharmaceutically acceptable preparation. In various embodiments, the kappa-opioid-receptor agonist may be devoid of activity on $5HT_2$ receptors, in particular $5HT_{2A}$ receptors, such that it does not produce mania. In various embodiments, the kappa-opioid-receptor agonist also has D2 agonist activity and, in particular, partial D2 agonist activity. In certain embodiments, the kappa-opioid-receptor agonist may be salvinorin A.

In various aspects of this embodiment, the system may include, in addition to the kappa-opioid-receptor agonist, either or both of a cannabinoid compound and Ketamine in a pharmaceutically acceptable preparation. The pharmaceutically acceptable preparation for the cannabinoid compound and/or ketamine may include the same carrier system in which the kappa-opioid-receptor agonist is administered and the substances may be administered together or separately in any combination thereof. Alternatively, the carrier system for the cannabinoid compound and/or ketamine may be different from that of the kappa-opioid-receptor agonist and the substances may be administered separately. In some embodiments, naltrexone is included.

DETAILED DESCRIPTION OF THE INVENTION

The present invention involves the treatment of neuropsychiatric conditions and disorders by administration of a substantially selective kappa-opioid-receptor agonist in a pharmaceutically acceptable preparation. Administration may be intranasal, transdermal or by inhalation. The substantially selective kappa-opioid-receptor agonists include, in particular, salvinorin A as well as derivatives of salvinorin A (see for example U.S. Pat. No. 7,687,538, which is incorporated by reference).

As used herein, the following terms are defined with the following meanings, unless explicitly stated otherwise.

*Salvia* is the genus name for annual, biennial, or perennial herbs in the mint family. *Salvia divinorum* is a species containing psychoactive compounds, of which the diterpenoid compound, salvinorin A, is the principal component. Salvinorin A is a selective kappa-opioid-receptor agonist (Roth et al., 2004) and D2 receptor partial agonist (Seeman et al., 2009) with no substantial effect on $5\text{-HTP}_{2A}$ receptors (Roth et al., 2004).

*Cannabis* is the genus name for the annual, dioecious flowering herb in which psychoactive constituents, principally tetrahydrocannabinol (THC), occur in the floral calyces. *Cannabis* plants include *Cannabis sativa*, *Cannabis indica*, and *Cannabis ruderalis* as well as various crosses and hybrids. There are also known strains of *Cannabis* including "drug" strains which contain high levels of THC and low levels cannabidiol (CBD) and "non-drug" strains such as hemp which contain high levels of CBD and low levels of THC.

The term "cannabinoid compound" as used herein, is intended to refer to terpenophenolic compounds that act on cannabinoid CB1 and/or CB2 receptors in cells including phytocannabinoids, endocannabinoids and synthetic cannabinoids. Phytocannabinoids can be found in *Cannabis* plants, endocannabinoids are produced naturally in the body and synthetic cannabinoids are man-made.

Examples of phytocannabinoids include cannabigerol (CBG), cannabichromene (CBC), cannabidiol (CBD), tetrahydrocannabinol (THC), cannabinol (CBN), cannabielsoin (CBE), iso-tetrahydrocannabinol (iso-THC), cannabicyclol (CBL) and cannabicitran (CBT).

The endocannabinoids bind to central (CB1) and peripheral (CB2) cannabinoid receptors. Examples of endocannabinoids include arachidonoylethanolamine (anandamide), 2-arachidonoylglycerol, 2-arachidonyl glyceryl ether, N-arachidonoyl dopamine and lysophosphatidylinositol.

Numerous synthetic cannabinoids have been made some of which have been used medicinally, for example, nabilone and rimonabant.

The term "cannabinoid compound" can also refer to any individual cannabinoid or combination of cannabinoid compounds such as the non-limiting example of THC+CBD+CBN or any other combination.

The term "about" when used before a numerical designation, e.g., pH, temperature, amount, concentration, and molecular weight, including range, indicates approximations which may vary by (+) or (−) 5%, 1% or 0.1%.

As used in the specification and claims, the singular form "a", "an" and "the" include plural references unless the context clearly dictates otherwise. For example, the term "a pharmaceutically acceptable carrier" may include a plurality of pharmaceutically acceptable carriers, including mixtures thereof.

The term "and/or" is intended to mean either or both of two components of the invention.

The term "subject," "individual" or "patient" is used interchangeably herein, and refers to a human.

The term "agonist," as used herein, refers to a moiety that interacts with and activates a receptor, and thereby initiates a physiological or pharmacological response characteristic of that receptor. The term "antagonist," as used herein, refers to a moiety that competitively binds to a receptor at the same site as an agonist (for example, the endogenous ligand), but which does not activate the intracellular response initiated by the active form of the receptor and can thereby inhibit the intracellular responses by an agonist or partial agonist. An antagonist does not diminish the baseline intracellular response in the absence of an agonist or partial agonist. The term "inverse agonist" refers to a moiety that binds to the endogenous form of the receptor or to the constitutively activated form of the receptor and which inhibits the baseline intracellular response initiated by the active form of the receptor below the normal base level of activity which is observed in the absence of an agonist or partial agonist.

The term "device," as used herein, refers to an apparatus or system capable of delivering a drug to patient in need thereof.

The term "in need of treatment" and the term "in need thereof" when referring to treatment are used interchangeably and refer to a judgment made by a caregiver (e.g. physician, nurse, nurse practitioner, that a patient will benefit from treatment.

The term "nostril," as used herein, is synonymous with "naris."

The term "nasal delivery", "intranasal delivery", "nasal administration" or "intranasal administration" refers to a route of administration wherein the pharmaceutical dosage form is taken to, or through, the nose (e.g., nasal cavity). Similarly, a "nasal delivery device" or an "intranasal delivery device' is intended to mean an apparatus that administers a drug into the nasal cavity. Non-limiting examples of intranasal administration include introduction of a solution or suspension in the form of a nasal spray or drops (direct instillation) or intranasal application of gel, emulsion or ointment.

The term "inhalation delivery" or "inhalation administration" refers to a route of administration wherein the pharmaceutical dosage form is taken into the airways and lungs by inhaling a gaseous, vaporized, or aerosolized drug preparation. Similarly, an "inhalation delivery device" is intended to mean an apparatus that administers a drug into the airways and lungs. The drug preparation may aerosolized using, e.g. a nebulizer.

The term "transdermal delivery" refers to a route of administration in which the pharmaceutical dosage form is taken up through the skin. Similarly, a "transdermal delivery device" is intended to mean any apparatus or system that administers a drug to be taken up through the skin.

The term "pharmaceutically acceptable," as used herein, refers to a component of a pharmaceutical composition that is compatible with the other ingredients of the formulation and not overly deleterious to the recipient thereof.

The term "carrier" refers to a diluent, adjuvant, excipient, or vehicle with which the therapeutic is administered and includes, but is not limited to such liquids and powders that are hydrophilic substances, hydrophobic substances and substances that possess both hydrophilic and hydrophobic properties such as emulsifiers.

By the term "substantially selective kappa-opioid-receptor agonist" it is meant that the agent has an affinity for kappa-opioid receptors and/or kappa-opioid biological activity, for example $EC_{50}$ (concentration of compound that gives half-maximal response) of at least 10-fold, at least 100-fold, at least 1000-fold or greater than that for mu- and delta-opioid receptors (see for example, Cunningham, 2011).

The term "substantially no effect on $5HT_2$ receptors" and, in particular "substantially no effect on $5HT_{2A}$ receptors" is intended to mean a compound has receptor affinity and/or elicits receptor mediated biological activity that is less than 0.1, less than 0.01, less than 0.001 or lesser than that for the kappa-opioid receptor (see for example Roth, 2004). Similarly, the term "produces substantially no manic effect" it is meant that the compound does not produce a meaningfully significant manic effect in a population of subjects.

The term "therapeutically effective amount," as used herein, refers to the amount of active compound or pharmaceutical agent that elicits the biological or medicinal response in a tissue, system, or individual that is being sought by a researcher, healthcare provider or individual.

Intranasal delivery devices are known in the art. Thus, any device suitable for delivery of drug to nasal mucosa may be used. Non-limiting examples of devices useful for the administration of liquid compositions include vapor devices (e.g., vapor inhalers), drop devices (e.g., catheters, single-dose droppers, multi-dose droppers, and unit-dose pipettes), mechanical spray pump devices (e.g., squeeze bottles, multi-dose metered-dose spray pumps, and single/duo-dose spray pumps), bi-directional spray pumps (e.g., breath-actuated nasal delivery devices), gas-driven spray systems/atomizers (e.g., single- or multi-dose HFA or nitrogen propellant-driven metered-dose inhalers, including traditional and circumferential velocity inhalers), and electrically powered nebulizers/atomizers (e.g., pulsation membrane nebulizers, vibrating mechanical nebulizers, and hand-held mechanical nebulizers). Non-limiting examples of devices useful for the administration of powder compositions (e.g., lyophilized or otherwise dried pooled compositions) include mechanical powder sprayers (e.g., hand-actuated capsule-based powder spray devices and hand-actuated powder spray devices, hand actuated gel delivery devices), breath-actuated inhalers (e.g., single- or multi-dose nasal inhalers and capsule-based single- or multi-dose nasal inhalers), and insufflators (e.g., breath-actuated nasal delivery devices).

Inhalation delivery devices are known in the art. Thus, any device suitable for delivery of drug to the lungs may be used. Non-limiting examples of suitable inhalation devices for inhalation include various types of modern inhalers based on different aerosolization technologies. For example, a metered-dose inhaler, a dry powder inhaler, a soft mist inhaler, or a nebulizer may be used. Metered-dose inhalers are typically pressurized, i.e. the active ingredient and optional inactive constituents are dispersed or dissolved in a liquid, pressurized propellant. A metered-dose inhaler typically comprises a canister which may be made of plastic, glass, aluminum, stainless steel, or any other suitable material; a metering valve allowing a metered quantity of the formulation to be dispensed with each actuation; and an actuator which is often combined with a mouthpiece to allow the subject to operate the device and direct the aerosol into the patient's lungs via the mouth.

Transdermal delivery devices are known in the art. Thus, any device suitable for delivery of drug across the skin of a patient may be used. Devices known in the art include reservoir type devices involving membranes that control the rate of drug release to the skin and devices where the drug is dispersed or dissolved in a matrix such as a pressure sensitive adhesive. Transdermal delivery devices may be made in the form of an article such as a tape, a patch, a sheet, a dressing or any other form known to those skilled in the art. Generally, the device may in the form of a patch of a size suitable to deliver a preselected amount of drug through the skin. Generally, the device will have a surface area of about 5 $cm^2$ to about 100 $cm^2$ and, in particular, about 10 $cm^2$ to about 40 $cm^2$.

Transdermal drug delivery devices typically involve a carrier (such as a liquid, gel, or solid matrix, or a pressure sensitive adhesive) into which a compound of the invention is incorporated.

For inhalation, or intranasal administration the preparation may contain a compound of the invention in a liquid carrier for aerosol application. In various embodiments, the composition may be in the form of an aqueous or non-aqueous solution, suspension, liposomal dispersion, emulsion, microemulsion or a combination thereof. The carrier can contain additives such as solubilizing agents, e.g., propylene glycol, surfactants, absorption enhancers such as lecithin (phosphatidylcholine) or cyclodextrin, mucoadhesives and/or preservatives such as parabens.

Methods well known in the art for making formulations may be found, for example, in Remington, 2000. Further, methods for formulating compounds for intranasal and transdermal administration, including for extending the presence in in the nasal cavity, creating various emulsions, combining with cyclodextrins and other agents to enhance solubility, creating prodrugs, analogs, and increasing bioavailability, etc. are well known. See, e.g., Bitter et al., 2011; Pastore et al., 2014.

The compounds of the present invention may be used for the treatment of neuropsychiatric disorders including affective disorders such as depression, bipolar disorder or anxiety disorder. Thus, the compounds may be used to treat abnormalities of mood or emotion including depression, bipolar disorder, dysthymia, post-traumatic stress disorder, schizoaffective disorder, schizophrenia and other psychotic disorders, anxiety disorders, panic disorder, traumatic stress disorders, phobic disorders, and personality disorders with abnormal mood, such as borderline personality disorder, schizoid and schizotypal disorders and suicide ideation.

The compounds of the present invention may also be used for treating addiction. Such addictions may be addiction to drugs, non-limiting examples of which may include nicotine, alcohol, cocaine, opioids, amphetamine, methamphetamine, heroin, morphine, phencyclidine, 3,4-methylenedioxy-methamphetamine, as well as other addictive substances. Additions may also include addictive behaviors, non-limiting examples of which may include eating, gambling, sex, pornography, videogames, work, exercise, spiritual obsession, self-harm, travel and shopping addiction.

Salvinorin A may be administered as *Salvia* divinorin or in a purified form of salvinorin A. When *Salvia* divinorin is administered, the dose is calculated in terms of the amount of salvinorin A administered from the preparation. The dose of salvinorin A when administered by inhalation may be in a range of from as low as about 50 µg, about 75 µg, about 100 µg, about 250 µg or about 400 µg up to about 500 µg, about 1000 µg, about 2000 µg, about 5000 µg or about 10,000 µg. The dose of salvinorin A when administered intranasally may be in a range of from as low as about 5 µg, about 7.5 µg, about 10 µg, about 25 µg or about 50 µg or about 100 µg up to about 200 µg, about 500 µg, about 1000 µg, about 2000 µg, about 5000 µg or about 10,000 µg. The dose of salvinorin A when administered transdermally may be in a range of from as low as about 5 µg, about 7.5 µg, about 10 µg, about 25 µg or about 50 µg or about 100 µg up to about 200 µg, about 500 µg, about 1000 µg, about 2000 µg, about 5000 µg or about 10,000 µg.

Ketamine may be administered intranasally as the hydrochloride at a dose in a range of from as low as about 5 µg, about 10 µg, about 20 µg, about 30 µg up to about 75 µg, about 125 µg, about 200 µg, or about 300 µg. In some embodiments, naltrexone is also administered to potentiate the effects of the ketamine administration.

The cannabinoid compound may be administered by combustion and inhalation of the floral calyces of a *Cannabis* plant or in a purified form of the cannabinoid compound. When *Cannabis* plant is administered, the dose is calculated in terms of the amount of the cannabinoid compound administered from the preparation. The dose of the cannabinoid compound when administered by inhalation may be in a range of from as low as about 200 µg, about 500 µg, about 1000 µg, about 2000 µg or about 5 µg up to about 10,000 µg, about 15,000 µg, about 20,000 µg, about 25,000 µg, about 50,000 µg, about 75,000 µg, about 100,000 µg, about 150,000 µg, or about 250,000 µg, or about 500,000 µg or about 750,000 µg, or about 1,000,000 µg, or about 1,500,000 µg or about 2,000,000 µg, or about 2,500,000 µg, or about 3,000,000 µg, or about 3,500,000 µg, or about 4,000,000 µg, or about 4,500,000 µg, or about 5,000,000 µg.

Administration may be once a day (q.d.), twice a day (b.i.d.), three times a day (t.i.d.), four times a day (q.i.d.) or at more or less frequent intervals such as once every other day (q.a.d.), once every third day, twice a week (bis in 7 d.), once a week (QWK), once every other week, etc. Alternatively, administration may be as needed (p.r.n.).

Preferred embodiments are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

Example 1. Salvinorin A Administration is Anxiolytic, Antidepressant and Motivationally Stimulating with No Manic Side Effects The effects of salvinorin A were evaluated in one subject with bipolar disorder following *Salvia divinorum* administration by combustion and inhalation at a dose of approximately 8 mg of enhanced leaf of 'regular strength' from a known online source (sagewisdom.com). After a brief, 2-5 minute period of mild hallucinations accompanied by euphoria, the subject experienced anxiolytic, antidepressant and motivationally stimulating effects for a period of 24 hours or greater with no manic side effects. It is noteworthy that this subject had experienced mania even on very small, sub-therapeutic doses of traditional antidepressants including celexa and sertraline—serotonin agonists and partial agonists. A slight tremor appeared shortly after administration, however, co-administration of *cannabis* by combustion and inhalation along with the *Salvia divinorum* eliminated the tremor. This method was repeated approximately 20 times with consistent results.

Co-administration of *cannabis* by combustion and inhalation and/or ketamine (ketamine hydrochloride, at varying doses, generally about 30 to about 75 mg) by intranasal administration along with *Salvia divinorum* by combustion and inhalation appeared to potentiate the anxiolytic and antidepressant effects of *Salvia divinorum* alone.

The subject also takes clonazepam, orally and/or sublingually, and has reported that clonazepam (at varying doses, generally about 1.5 mg, b.i.d. and occasionally, about 0.5 mg up to about 2.5 mg p.r.n.), along with co-administration of *cannabis* by combustion and inhalation and/or ketamine by intranasal administration with *Salvia divinorum* by combustion and inhalation appeared to potentiate the anxiolytic and antidepressant effects of the *Salvia divinorum* alone and helped to further alleviate any anxiety, tremor or any other side effect before, during or after administration of the *Salvia divinorum*.

Example 2. Effects of Intranasal or Transdermal Administration of Salvinorin A on Behavioral Activity Preparation of the intranasal and transdermal salvinorin A is by known methods. See, e.g., Bitter et al., 2011; Pastore et al., 2015.

Following intranasal or transdermal delivery of salvinorin A at 3 separate dosages, with a negative control administered vehicle only, rats are monitored for a total of 40 minutes by an experimenter who is blinded to condition. Signs of altered behavior, including staring, immobility, increased or decreased response to stimuli (e.g. tactile, auditory), and changes in locomotor patterns are recorded.

For each method of administration, a total of 48 Sprague-Dawley male & female CD rats ~45 days old are utilized (Table 1).

TABLE 1

Summary of Treatment Groups

| Group | Treatment | Purpose | Number ♂ | ♀ |
|---|---|---|---|---|
| T-1 | Concentration 1 | Test Article (Dose 1) | 6 | 6 |
| T-2 | Concentration 2 | Test Article (Dose 2) | 6 | 6 |
| T-3 | Concentration 3 | Test Article (Dose 3) | 6 | 6 |
| C-1 | Vehicle only | Negative Control | 6 | 6 |

Following a 5-7 day acclimation phase, rats are randomly divided into 4 groups (C1, T1, T2, T3; Table 1) and receive intranasal or transdermal administration of the appropriate dosage of Compound X.

Visual (real-time) monitoring is performed for 10 minutes pre-administration and 30 minutes post-administration of the compound.

Animals are observed in real time to assess behavioral anomalies, with 4 animals monitored simultaneously (1 from each condition). Periods of staring, increased or decreased response to stimuli (e.g. tactile, auditory), and any other unusual behaviors are noted. Animals are also video recorded, with locomotor activity, rearing, grooming, and periods of immobility assessed using the AnyMaze™ behavioral scoring system (Stoelting Co., Wood Dale Ill. 60191 US). All behavioral evaluations are performed by an experimenter blinded to condition. The following 2 phases are used to allow for within and between animal comparisons:

Parametric data is evaluated using 2-way ANOVA (SEX by TREATMENT). Statistically significant main effects are further investigated using Tukey's post hoc analysis. Non-parametric analyses are assessed using a Kruskal-Wallis test with Dunn-Bonferroni pairwise comparisons for post hoc analysis. Significance level for all tests is $p \leq 0.05$.

Example 3. Effects of Intranasal or Transdermal Administration of Salvinorin A on Anxiety Salvinorin A is administered intranasally or transdermally to rats at one of 3 different dose levels (1, 2 or 3). In addition to a normal control, there is both a positive and a negative control group. For the positive control, rats receive a 5 mg/kg injection (i.p.) of tracazolate, a non-benzodiazepine anxiolytic compound (Thompson et al., 2002). As a negative control, FG7142 (5 mg/kg i.p.) is administered to produce anxiogenic behavior (Pellow and File, 1986). The normal control group receives an i.p. injection of an equivalent volume (2 ml/kg) of sterile saline. All control groups also receive an equivalent volume of vehicle delivered in an identical manner to that used for the test article (i.e. intranasal or transdermal administration).

A total of 60 Sprague-Dawley male CD rats ~45 days old are utilized for each administration method (Table 2).

TABLE 2

Summary of Treatment Groups

| Group | Treatment | Purpose | Number |
| --- | --- | --- | --- |
| T-1 | Concentration 1 | Test Article (Dose 1) | 10 |
| T-2 | Concentration 2 | Test Article (Dose 2) | 10 |
| T-3 | Concentration 3 | Test Article (Dose 3) | 10 |
| Veh | Vehicle | Normal Control | 10 |
| Pos | Tracazolate | Anxiolytic | 10 |
| Neg | FG7142 | Anxiogenic | 10 |

Following a minimum 7 day acclimation phase, rats are randomly divided into 6 groups (T1, T2, T3, Veh, Pos, Neg; Table 2).

Forty-five minutes prior to behavioral testing, an i.p. injection is administered to all animals in a volume of 2 ml/kg as follows: rats in the anxiolytic control group, receive tracazolate (5 mg/kg), a pyrazolopyridine that reduces anxiety-like behaviors in rodents (Pellow and File, 1986), an effect believed to result from allosteric modulation of extrasynaptic GABAA receptor function (Thompson et al., 2002; Belelli et al., 2009). As an anxiogenic control, a second group of rats receive FG7142 (N-methyl-β-carboline-3-carboxamide), a beta-carboline that acts as a partial inverse agonist at the benzodiazepine allosteric site (Evans and Lowry, 2007) and produces demonstrated increases in anxiety-like behaviors in various tasks (Thompson et al., 2002; Arrant et al., 2013). Rats in experimental groups (i.e. those who have received a test compound), as well as rats in the normal control group receive an injection of sterile saline.

Thirty minutes prior to behavioral testing, rats in test article groups receive intranasal or transdermal administration of salvinorin A at one of the 3 dosage levels. Animals in the normal control group receive administration of vehicle only in a volume equivalent to that utilized for the experimental animals. Following treatment as per its assigned group, each rat is tested in either the Open Field (OF) test or the Elevated Plus Maze (EPM) to assess anxiety-like behaviors. One week later, the same rats receive the same group treatment (experimental or control) and undergo testing in the paradigm not yet experienced (i.e. OF or EPM). All tests are video recorded for scoring and documentation purposes.

Ultrasonic vocalizations (USVs) is also recorded and analyzed to provide an additional level of anxiety-related measures.

The following behavioral tests are performed:

Elevated Plus test (Bailey and Crawley, 2009)—The arena for this test consists of four arms, two with sidewalls, and two open (a "plus" configuration), thus providing a measure of anxiety associated with open space, unprotected regions. The maze is elevated ~2 feet above the floor. Rats are started in the center (neutral) zone of the test, and behavioral measures include latency to enter and percent of time spent in the closed arms as recorded during a 10 minute trial.

Open Field test (Gould et al., 2009)—The open field test allows assessment of activity levels, locomotion, and anxiety-related behaviors. Rats are started in the center of the arena (~4.5 foot diameter), and measures during a 10 minute test period may include: latency to reach the outer wall region, time spent in thigmotaxic behavior, number of entries into and time spent in the center region, distance traveled, average speed in each region, number and time spent rearing, number and time spent grooming, and comparison of activities during the first and last minute, and first and last half of the task.

Ultrasonic Vocalizations—Ultrasonic vocalization emissions are recorded during testing, with number, duration, and frequency range of calls assessed to provide an additional measure of affective state during testing. See also Bourin, 2015; and Campos et al., 2013.

Example 4. Antidepressant Effects of Intranasal or Transdermal Administration of Salvinorin A For confirming its antidepressant effects, salvinorin A is administered intranasally or transdermally to rats at one of 3 different dose levels (1, 2 or 3), with a control group that receives an equivalent volume of vehicle delivered in an identical fashion to the test article.

A total of 40 Sprague-Dawley male CD rats ~45 days old are utilized for each administration method (Table 3).

TABLE 3

Summary of Treatment Groups

| Group | Treatment | Purpose | Number |
| --- | --- | --- | --- |
| T-1 | Concentration 1 | Test Article (Dose 1) | 10 |
| T-2 | Concentration 2 | Test Article (Dose 2) | 10 |
| T-3 | Concentration 3 | Test Article (Dose 3) | 10 |
| Veh | Vehicle | Normal Control | 10 |

Following the acclimation phase, rats are randomly divided into 4 groups (T1, T2, T3, Veh; Table 3).

On the day of the test phase, ultrasonic vocalization (USV) emissions are recorded from each rat at 3 time points—prior to compound administration, immediately following compound administration, and immediately after the test phase. Thirty minutes prior to the test phase, rats in experimental groups receive intranasal or transdermal administration of the appropriate dosage of salvinorin A (T-1, T-2, or T-3). Rats in control groups receive an equivalent volume of vehicle delivered in an identical manner.

Following treatment as per its assigned group, each rat is tested in the Forced Swim Test (FST) to assess depressive behaviors. All tests are video recorded for scoring and documentation purposes.

The forced swim test is based on a rodent's aversion to water, and subsequent desire to try and escape when submerged. To induce the model, rats are placed in an inescapable water-filled container (~8" diameter×20" deep) for 15 minutes (pre-test phase). Duration of struggling/climbing, immobility, and swimming activities are measured during each 5 minute block to provide a baseline evaluation. Twenty-four hours later, rats are once again placed in an inescapable water-filled container, and measures are recorded for 5 minutes (test phase).

To provide an additional level of affective state, USV emissions are recorded for 5 minutes prior to, and following, the pre-test phase. In addition, USVs will be recorded on the testing day for 5 minutes prior to the test phase, 5 minutes immediately following compound administration, and 5 minutes following the test phase.

Parametric data is evaluated using ANOVA, with repeated measures utilized where appropriate. Statistically significant main effects are further investigated using Tukey's post hoc analysis. Non-parametric analyses will be assessed using a Kruskal-Wallis test with Dunn-Bonferroni pairwise comparisons for post hoc analysis. The Friedman test will be used to evaluate non-parametric repeated measures data. Significance level for all tests will be $p \leq 0.05$.

See also Bogdanova et al., 2013; Krishnan and Nestler, 2011; Abelaira et al., 2013; Gould and Einat, 2007; and Abulseoud et al., 2014.

Example 5. Effects of Intranasal or Transdermal Administration of Salvinorin A on Chronic Depression Chronic exposure to mild, unpredictable stress is used as a rodent model of long-term depression. This paradigm results in decreased consumption of sweetened water, a treat that is generally rewarding to rats.

For confirming its effects on chronic depression, salvinorin A is administered intranasally or transdermally to rats at one of 3 different dose levels (1, 2 or 3), with a control group that receives an equivalent volume of vehicle delivered in an identical fashion to the test article.

A total of 60 male Wistar CD rats ~45 days old are utilized for each administration method (Table 4).

TABLE 4

Summary of Treatment Groups

| Group | Treatment | Stress | Purpose | Number |
|---|---|---|---|---|
| A | Compound X1 | Yes | Test Article Dose 1 | 12 |
| B | Compound X2 | Yes | Test Article Dose 2 | 12 |
| C | Compound X3 | Yes | Test Article Dose 3 | 12 |
| D | Vehicle | Yes | Negative Control | 12 |
| E | Vehicle | No | Normal Control | 12 |

Starting 24 hours after arrival in the facility, rats will be acclimated to a sugar water solution (1% sucrose), to avoid neophobic behaviors during the testing period. Baseline measures of sucrose preference will be obtained prior to model induction.

Upon study initiation, rats are randomly divided into 5 groups (X1, X2, X3, Negative Control, Normal Control; Table 4).

Chronic mild stress protocols are performed for a 6 week period as outlined below, with a 24 hour sucrose preference test administered weekly.

For the final 3 weeks of the chronic mild stress protocol, each rat receives daily salvinorin A administration as per its assigned group. Control (non-stressed) rats receive an equivalent volume of vehicle, delivered in an identical fashion as the test article. As during the induction phase, a 24 hour sucrose preference test is administered weekly.

To produce a model of chronic depression, a series of mild, unpredictable stressors will be utilized, with protocols adapted from previous literature (Harden et al., 2012; Lopez-Lopez et al., 2016; Papp et al., 1996). A decrease in consumption of a rewarding treat (sugar water) over a 24 hour presentation period (tested once per week; see Behavioral Testing section below) is considered indicative of depressed behavior (anhedonia).

Stressors to be utilized include a 16 hour food deprivation period, 15 hour water deprivation followed by 1 hour empty water bottle presentation, 36 hours continuous light, 9 hours wet cage bedding, 15 minute immersion in cold water, 5 hour foreign object presentation (some objects will restrict movement in cage), 5 hours inclined (45° cage), and 3 hours noise (~40 dB) to be presented with or without other stressors.

Prior to model induction, a baseline level for sucrose preference is established over a 24 hour period as outlined below.

Sucrose Preference Testing—Once per week, for a 24 hour period, regular water bottles will be replaced with two pre-weighed bottles, one containing regular water, and one with a 1% sucrose solution (sugar water). After 24 hours, bottles will be weighed again, and consumption of each will be recorded. No stressors will be administered during or for 12 hours prior to this time period.

Parametric data will be analyzed using ANOVA, with repeated measures where appropriate. Statistically significant main effects will be further investigated using Tukey's post hoc analysis. Significance level for all tests will be $p \leq 0.05$.

See also Lynch et al., 2010 and Planeta, 2013.

Example 6. Effects of Intranasal or Transdermal Administration of Salvinorin A on Addictive Behaviors Reinforcing effects of drugs of abuse are believed to play a key role in substance abuse and addiction; paradigms that measure drug reinforced behaviors allow for evaluation of compounds that may interfere with these processes. The conditioned place preference paradigm provides assessment of a drug's rewarding effects, and when used with a known addictive substance, the paradigm allows for screening of compounds with potentially therapeutic benefits.

For confirming its effects on addictive behaviors, salvinorin A is administered intranasally or transdermally to rats at one of 3 different dose levels (1, 2 or 3), with a control group that receives an equivalent volume of vehicle delivered in an identical fashion to the test article.

Control groups are saline only exposure (negative control) or cocaine only exposure (positive control) plus administration of an equivalent volume of vehicle delivered in an identical fashion to the test article (i.e. intranasal administration).

A total of 50 Sprague-Dawley male SD rats ~45 days old upon arrival in the facility will be utilized for each administration method (Table 5).

TABLE 5

Summary of Treatment Groups

| Group | Treatment | Purpose | Number |
|---|---|---|---|
| A | Compound X1 | Test Article Dose 1 | 10 |
| B | Compound X2 | Test Article Dose 2 | 10 |
| C | Compound X3 | Test Article Dose 3 | 10 |
| D | Saline/vehicle | Negative Control | 10 |
| E | Cocaine/vehicle | Positive Control | 10 |

Upon study initiation, rats are randomly divided into 5 groups (X1, X2, X3, Pos, Neg; Table 5). All phases of the study are performed under reverse light cycle.

One day prior to the habituation phase of the study, rats receive a single intraperitoneal (i.p.) injection of saline prior to being returned to the home cage.

During habituation, rats are exposed to the testing apparatus for 15 minutes per day for 3 days.

During the conditioning phase, each animal is administered the appropriate compound (cocaine or saline alternated over days) and immediately be placed in the associated chamber (drug or vehicle as appropriate) of the apparatus for 30 minutes per day for 8 consecutive days. Saline control animals receive saline only each day, with chamber presentation alternated over days.

On the testing day, 24 hours after the last conditioning trial, each rat receives intranasal or transdermal compound administration as per its assigned group, and is tested at the post-administration time point as specified by the sponsor to determine the effects of the various dosage levels of the compound on cocaine-induced CPP. All tests are video recorded for scoring and documentation purposes by experimenters blinded to rat condition.

An i.p. injection of either cocaine (20 mg/kg) or saline in a maximum volume of 10 ml/kg will be administered to rats during conditioning trials as specified in the behavioral testing section below.

The following behavioral tests are performed:

Cocaine-induced Conditioned Place Preference test (CPP) (Buccafusco, 2009; Galaj et al. 2014)—This test provides an assessment of the degree of reward associated with cocaine administration. The testing apparatus consists of two compartment chambers plus a center "tunnel" area (unforced choice) separated by doors, with the two larger outer chambers varying in both color (e.g. black vs white) and floor texture (e.g. horizontal grid vs cross-grid). The center connecting chamber has no special characteristics, is not paired with any compound and is not accessible during habituation. Measures that are evaluated include time spent in each chamber, first chamber chosen, chamber entries, speed, and distance traveled.

There are three stages:

1) Habituation—rats are placed in the test apparatus and allowed free access for 15 minutes per day for a total of 3 days to eliminate novelty as a confounding variable. Time spent in each compartment is recorded to determine compartment preference prior to conditioning.

In order to habituate rats to injections, an i.p. injection of saline is administered one day prior to the first apparatus exposure. Following this injection, rats are placed back in their home cage.

2) Conditioning—rats are conditioned over 8 consecutive days, with cocaine administration repeated once every other day for a total of 4 cocaine conditioning days. On cocaine conditioning days, rats are given an injection of cocaine (20 mg/kg i.p.), and are immediately confined for 30 minutes in the compartment for which they showed the least preference during the habituation stage (biased procedure). On alternate days, rats are given an injection of saline, and are confined to the opposite chamber to that utilized during cocaine conditioning. The order of cocaine conditioning is counterbalanced across rats. One group of rats (negative control) will receive a daily injection of vehicle only and alternately be exposed to each compartment.

3) Testing—24 hours following the last conditioning session, all rats receive intranasal administration of the appropriate test article dose or an equivalent volume of vehicle. Cocaine-induced CPP is assessed by placing the rat in the center compartment and allowing free access to the entire apparatus for 15 minutes. Time spent in each compartment is measured.

Parametric data will be analyzed using ANOVA. Statistically significant main effects are further investigated using Tukey's post hoc analysis. Significance level for all tests will be $p \leq 0.05$.

REFERENCES

Abelaira et al., Animal models as tools to study the pathophysiology of depression, *Revista Brasileira de Psiquiatria* 35:S112-S120 (2013).

Abulseoud et al., Lateral hypothalamic kindling induces manic-like behavior in rats: a novel animal model, *International J. Bipolar Disorders* 2:7 (2014).

Afridi, A randomized controlled trial of intranasal ketamine in migraine with prolonged aura, *Neurology* 80:642-647 (2013).

Andrade, Intranasal Drug Delivery in Neuropsychiatry: Focus on Intranasal Ketamine for Refractory Depression, *J. Clin. Psychiatry,* 76:628-631 (2015).

Arrant, A. E., Schramm-Sapyta, N. L., Kuhn, C. M. *Behavioural Brain Research* 256: 119-127 (2013).

Bailey and Crawley, Chapter 5 in Methods of Behavior Analysis in Neuroscience, $2^{nd}$ Ed., J. J. Buccafusco, editor (2009).

Belelli, D., Harrison, N. L., Maguire, J., Macdonald, R. L., Walker, M. C., Cope, D. W. *The Journal of Neuroscience* 29(41): 12757-12763 (2009).

Bitter et al., Nasal Drug Delivery in Humans, *Curr. Prol. Dermatol.* 40:20-35 (2011).

Bogdanova, O. V., Kanekar, S., D'Anci, K. E., Renshaw, P. F. *Physiology and Behavior,* 118: 227-239 (2013).

Bourin, Animal models for screening anxiolytic-like drugs: a perspective, *Dialogues in Clinical Neuroscience* 17:295-303 (2015).

Buccafusco, J. J. Ed. Methods of Behavior Analysis in Neuroscience (2nd ed). CRC Press (2009).

Campos et al., Animal models of anxiety disorders and stress. *Revista Brasileira de Psiquiatria* 35:S101-S111 (2013).

Clark, Treatment-refractory depression: a case of successful treatment with intranasal ketamine 10%, *Ann Clin Psychiatry* 26:145 (2014).

Cunningham et al., Neuropharmacology of the Naturally Occurring κ-Opioid Hallucinogen Salvinorin A, *Pharmacol Rev* 63:316-347 (2011).

Dhuria et al., Intranasal delivery to the central nervous system: mechanisms and experimental considerations, *J Pharm Sci.,* 99:1654-1673 (2011).

Djupesland et al., The nasal approach to delivering treatment for brain diseases: an anatomic, physiologic, and delivery technology overview, Therapeutic Delivery 5, 709-733 (2014).

Evans, A. K., Lowry, C. A. *CNS Drug Reviews* 13(4): 475-501 (2007).

Galaj, E., Manuszak, M., Arastehmanesh, D., Ranaldi, R. Beh Brain Research. 272: 279-285 (2014).

Giroud et al., *Salvia divinorum*: an hallucinogenic mint which might become a new recreational drug in Switzerland, *Forensic Sci. Int.* 112:143-150 (2000).

Gould and Einat, 2007, Animal models of bipolar disorder and mood stabilizer efficacy: a critical need for improvement, *Neurosci. Biobehav. Rev.* 31:824-831 (2007).

Gould, T. D., Dao, D. T., Kovacsics, C. E. *Neuromethods* v42, Humana Press: p 1-20 (2009).

Graudins et al., The PICHFORK (Pain in Children Fentanyl or Ketamine) trial: a randomized controlled trial comparing intranasal ketamine and fentanyl for the relief of moderate to severe pain in children with limb injuries, *Ann Emerg Med.* 65:248-254 (2015).

Harden et al., Antidepressive effects of the κ-opioid receptor agonist Salvinorin A in a rat model of anhedonia, *Behav Pharmacol.* 23:710-715 (2012).

Ita, Transdermal Delivery of Drugs with Microneedles—Potential and Challenges, *Pharmaceutics* 7, 90-105 (2015).

Johnson et al., Human psychopharmacology and dose-effects of Salvinorin A, a kappa-opioid agonist hallucinogen present in the plant *Salvia divinorum Drug Alcohol Depend,* 115:150-155 (2011).

Krishnan and Nesler, Animal models of depression: molecular perspectives, *Curr. Top. Behav. Neurosci.* 7:121-147 (2011).

Krystal et al., Potentiation of low dose ketamine effects by naltrexone: potential implications for the pharmacotherapy of alcoholism, *Neuropsychopharmacology* 31:1793-1800 (2006).

Lapidus, A randomized controlled trial of intranasal ketamine in major depressive disorder, *Biol Psychiatry* 76:970-976 (2014).

Lopez-Lopez, A. L., Jaime, H. B., Escobar-Villaneuva, M., Padilla, M. B., Palacios, G. V., Aguilar, F. J. *Physiology & Beh.* 161: 15-23 (2016).

Lynch et al., Animal models of substance abuse and addiction: Implications for science, animal welfare, and society, *Comparative Medicine* 60:177-188 (2010).

Maqueda et al., Salvinorin-A Induces Intense Dissociative Effects, Blocking External Sensory Perception and Modulating Interoception and Sense of Body Ownership in Humans, *Int. J. of Neuropsychopharmacol.,* 1-14 (EPub ahead of print)(2015).

Mendelson et al., Lack of effect of sublingual Salvinorin A, a naturally occurring kappa opioid, in humans: a placebo-controlled trial *Psychopharmacol,* 214:933-939 (2011).

Morani et al., Effect of kappa-opioid receptor agonists U69593, U50488H, spiradoline and Salvinorin A on cocaine-induced drug-seeking in rats, *Pharmacol Biochem Behav* 94: 244-249 (2009).

Orton et al., Salvinorin A: A Mini Review of Physical and Chemical Properties Affecting Its Translation from Research to Clinical Applications in Humans, *Transl. Perioper. Pain Med.,* 1:9-11 (2014).

Ott, Ethnopharmacognosy and Human Pharmacology of *Salvia divinorum* and Salvinorin A, *Curare* 181:103-129 (1995).

Papp, M., Moryl, E., Willner, P. *Eur J Pharmacology.* 196:129-136 (1996).

Pastore et al., Transdermal patches: history, development and pharmacology, *British J. Pharmacol.* 172:2179-2209 (2015).

Paudel et al., Challenges and opportunities in dermal/transdermal delivery, *Ther. Deliv.* 1:109-131 (2010).

Pellow, S., File, S. E., *Pharmacology Biochemistry & Behavior* 24: 525-529 (1986).

Planeta, Animal models of alcohol and drug dependence, *Revista Brasileira de Psiquiatria* 35:S140-S146 (2013).

Prevatt-Smith et al, Potential Drug Abuse Therapeutics Derived from the Hallucinogenic Natural Product Salvinorin A, *Med. Chem. Comm.* 2:1217-1222 (2011).

Remington: The Science and Practice of Pharmacy" (20th ed.), ed. A. R. Gennaro, 2000, Lippincott Williams & Wilkins.

Roth et al., Salvinorin A: A potent naturally occurring nonnitrogenous κ opioid selective agonist, *PNAS* 99:11934-11939 (2004).

Seeman et al., Dopamine D2 High receptors stimulated by phencyclidines, lysergic acid diethylamide, Salvinorin A, and modafinil, *Synapse* 63:698-704 (2009).

Siebert, *Salvia divinorum* and Salvinorin A: new pharmacologic findings, *J Ethnopharmacol.* 43:53-56 (1994).

Thompson, S., Wingrove, P. B., Connelly, L., Whiting, P. J., Wafford, K. A. *Molecular Pharmacology* 61(4): 861-869 (2002).

Valdes, *Salvia divinorum* and the unique diterpene hallucinogen, Salvinorin (divinorin) A, *J. Psychoactive Drugs* 26, 277-283 (1994).

Yatham et al., Brain serotonin-2 receptors in acute mania, *The British J. Psych.* 196:47-51 (2010).

Yeaman, Sub-dissociative-dose intranasal ketamine for moderate to severe pain in adult emergency department patients, *Emerg Med Australas* (2014).

In view of the above, it will be seen that several objectives of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A method of treating tremor caused by transdermal, transnasal or inhalation administration of salvinorin A in a patient with depression, bipolar disorder or anxiety disorder, the method comprising:

administering ketamine and/or a cannabinoid in a pharmaceutically acceptable preparation sufficient to treat the tremor.

2. The method of claim 1, wherein the pharmaceutically acceptable preparation comprises an aqueous or non-aqueous solution, suspension, liposomal dispersion, emulsion or microemulsion formulation.

3. The method of claim 1, wherein the affective disorder is depression.

4. The method of claim 1, wherein the affective disorder is anxiety disorder.

5. The method of claim 1, wherein both a cannabinoid compound and ketamine are administered in the pharmaceutically acceptable preparation.

6. The method of claim 1, wherein the affective disorder is bipolar disorder.

7. The method of claim 1, wherein the ketamine and/or the cannabinoid is administered intranasally.

8. The method of claim 1, wherein ketamine is administered without a cannabinoid.

9. The method of claim 1, wherein a cannabinoid is administered without ketamine.

10. The method of claim 1, further comprising administration of clonazepam.

11. The method of claim 6, wherein the patient experiences mania when administered a serotonin agonist or partial agonist.

12. The method of claim 11, wherein the serotonin agonist or partial agonist is celexa or sertraline.

13. The method of claim 1, wherein the salvinorin A is administered intranasally.

14. The method of claim 1, wherein the salvinorin A is administered transdermally.

15. The method of claim 1, wherein the salvinorin A is administered by combustion and inhalation.

16. The method of claim 1, wherein the cannabinoid is administered by inhalation.

17. The method of claim 1, wherein a vaporized preparation is inhaled.

18. The method of claim 9, wherein the cannabinoid is administered by combustion and inhalation.

* * * * *